(12) United States Patent
Renard

(10) Patent No.: US 9,636,365 B2
(45) Date of Patent: May 2, 2017

(54) ANTIBACTERIAL FOOD COMPOSITION

(75) Inventor: Loïc Renard, Rueil Malmaison (FR)

(73) Assignee: NUTRIVERCELL, Evry (FR)

( * ) Notice: Subject to any disclaimer, the term of this patent is extended or adjusted under 35 U.S.C. 154(b) by 0 days.

(21) Appl. No.: 13/391,501

(22) PCT Filed: Apr. 1, 2010

(86) PCT No.: PCT/FR2010/050627
§ 371 (c)(1),
(2), (4) Date: May 7, 2012

(87) PCT Pub. No.: WO2011/020957
PCT Pub. Date: Feb. 24, 2011

(65) Prior Publication Data
US 2012/0214781 A1 Aug. 23, 2012

(30) Foreign Application Priority Data
Aug. 21, 2009 (FR) ..................................... 09 55738

(51) Int. Cl.
*A61K 35/644* (2015.01)
*A61K 36/45* (2006.01)
*A23L 33/105* (2016.01)

(52) U.S. Cl.
CPC .......... *A61K 35/644* (2013.01); *A23L 33/105* (2016.08); *A61K 36/45* (2013.01)

(58) Field of Classification Search
CPC ...... A23L 1/3002; A61K 35/644; A61K 36/45
USPC ....................................................... 424/539
See application file for complete search history.

(56) References Cited

U.S. PATENT DOCUMENTS

2005/0158381 A1 7/2005 Aldritt et al.

FOREIGN PATENT DOCUMENTS

| EP | 1 902 721 | 3/2008 |
| EP | 1902721 A1 * | 3/2008 |
| EP | 1 913 951 | 4/2008 |
| WO | WO 02/062362 | 8/2002 |

OTHER PUBLICATIONS

Famine Mary, URImel Nov. 26, 2008 [retrieved on Oct. 19, 2012]. Retrieved from the Internet <http://web.archive.org/web/20081126045946/http://www.famillemary.fr/boutique_us/fiche_produit.cfm?url=&type=179&ref=web_084601&code_lg=lg_us&pag=1&num=3&tri=0&marq=0>).*

Marcucci, Propolis: chemical composition, biological properties and therapeutic activity. Apidologie, vol. 26 (1995) pp. 83-99.*
Shankar et al., Zinc and immune function: the biological basis of altered resistance to infection. American Journal of Clinical Nutrition, vol. 68 Supp. (1998) pp. 447S-463S.*
Chandra et al., Trace element regulation of immunity and infection. Nutrition Research, vol. 2 (1982) pp. 721-733.*
Hudson, Treatment and prevention of bladder infections. Alternative and Complementary Therapies, (Dec. 2006) pp. 297-302.*
Iron (II) Sulfate. Wikipedia, 2013 [retrieved on Jul. 8, 2013]. Retrieved from the Internet: <URL: https://en.wikipedia.org/wiki/Iron(II)_sulfate>.*
Zinc oxide. Wikipedia, 2013 [retrieved on Jul. 8, 2013]. Retrieved from the Internet: <URL:https://en.wikipedia.org/wiki/Zinc_oxide>.*
Calcium Ascorbate. Wikipedia, 2013 [retrieved on Jul. 8, 2013]. Retrieved from the Internet: <URL:https://en.wikipedia.org/wiki/Calcium_ascorbate>.*
Pathogenic Bacteria. Wikipedia, 2013 [retrieved on Jul. 3, 2013]. Retrieved from the Internet: <URL: http://en.wikipedia.org/wiki/Pathogenic_bacteria>.*
Celik et al., Caffeic acid phenethyl ester suppresses oxidative stress in *Escherichia coli*-induced pyelonephritis in rats. Molecular and Cellular Biochemistry, vol. 297 (2007) pp. 131-138.*
Propolis PR-007. Datasheet [online]. Draper's Super Bee Apiaries, Inc., May 2009 [retrieved on Jan. 4, 2016]. Retrieved from the Internet<URL: http://www.draperbee.com/catalog/page6.htm>.*
International Search Report for PCT/FR2010/050627.
Max Shrem: "Famille Mary: Offering pharmaceuticals made from honey" Slashfood Jun. 18, 2008, pp. 1-8, XP002574073, Retrieved from the Internet: URL:http://www.slashfood.com/2008/06/18/fa_mille-mary-offering-pharmaceuticals-made-f_rom-honey/; [retrieved on Mar. 19, 2010], p. 3.
Bruyere et al: "Utilisation de la canneberge dans les infections urinaires recidivantes" Medecine et Maladies Infectieuses, Societe Francaise D'Editions Medicales, Paris, FR, vol. 36, No. 7, (Jul. 1, 2006), pp. 358-363.
Uzel A et al: "Chemical compositions and antimicrobial activities of four different Anatolian propolis samples" Microbiological Research, Fischer, Jena, DE, vol. 160, No. 2, (Apr. 25, 2005), pp. 189-195.
Popova M et al: "Antibacterial activity of Turkish propolis and its qualitative and quantitative chemical composition" Phytomedicine, Gustav Fischer Verlag, Stuttgart, vol. 12, No. 3, (Mar. 22, 2005) pp. 221-228.
Lavigne, et al., "Propolis can potentialise the anti-adhesion activity of proanthocyanidins on uropathogenic *Escherichia coli* in the prevention of recurrent urinary tract infections", 2011, pp. 1-7, vol. 4, No. 522, BMC Research Notes.

* cited by examiner

*Primary Examiner* — Kara Johnson
(74) *Attorney, Agent, or Firm* — B. Aaron Schulman, Esq.; Stites & Harbison, PLLC

(57) ABSTRACT

The present invention relates to an antibacterial food composition comprising a Propolis extract and a *Vaccinium macrocarpon* cranberry extract.

27 Claims, 2 Drawing Sheets

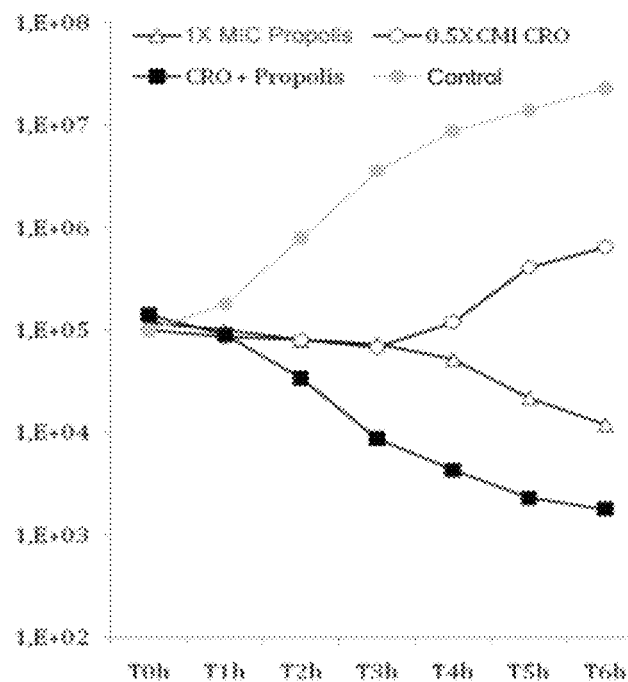
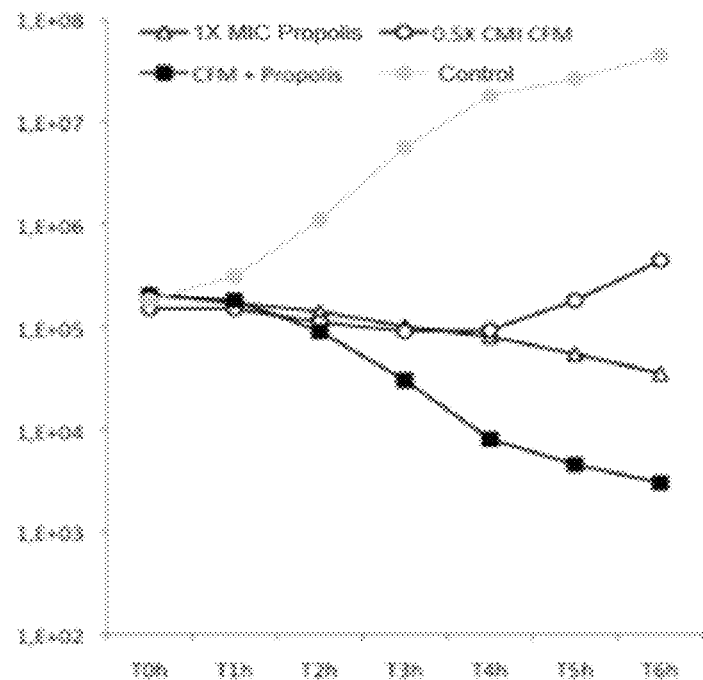

ANTIBACTERIAL FOOD COMPOSITION

The present invention relates to an antibacterial food composition comprising a propolis extract and a *Vaccinium macrocarpon* extract. The invention more particularly relates to an antibacterial food composition intended for treating acute or chronic bacterial infections. The invention also relates to the combination of a propolis extract or of a composition comprising a propolis extract and a *Vaccinium macrocarpon* extract, with certain classes of antibiotics.

Urinary infections are extremely frequent. They come after respiratory infections at the second rank of consultation motives and of prescription of antibiotics. They are easily recurrent notably in women and those having a neurogenic bladder. The microbial agent responsible for more than 90% of these urinary infections is *Escherichia coli*, a commensal bacterium of the digestive tract which may become pathogenic by acquiring pathogenicity islets.

Their management by conventional therapy and in particular by resorting to antibiotics, has been generalized but however proves to be less and less satisfactory, given the increasing resistance of bacteria to these antibiotic agents.

In order to solve this problem, one of the solutions is to decrease the bacterial population by mechanisms very different from those of antibiotics and which therefore act independently of the resistance and virulence of bacteria.

*Vaccinium macrocarpon* is a fruit plant corresponding to cranberry or large cranberry. The extract of cranberry *Vaccinium macrocarpon* is known for its bacterial anti-adhesion properties which are exploited in the treatment of many urinary infections in order to combat development of bacteria. The consumption of *Vaccinium macrocarpon* cranberry juice would prevent urinary infections (JP Lavigne, Clin. Microbiol. Infect. 2007, p1-5). The Tournay corporation markets extracts under the name of EXOCYAN®, characterized by their proanthocyanidin (PAC) content, standardized to values from 10 to 50% according to the vanillin measurement method.

Patent application EP 1 902 721 describes the association of a *Vaccinium macrocarpon* extract and a urinary antibacterial agent against Gram$^+$ and Gram$^-$ bacteria in a composition intended to control urinary infections and to be selective so as not to cause disappearance of the bacterial flora normally present in the urethra.

Both bacteriostatic and bactericidal properties of propolis on many microbial strains, and in particular on *Escherichia coli*, are also known.

Three nutritional supplements intended for treating urinary infections are marketed under the names of Urimel by the Famille Mary corporation, "Biophyto.com Infection Urinaire gènes urinaires fréquentes récidivantes" by Biophyto.com and of Uriprop by the Laboratoire Lax corporation and comprise a cranberry extract associated with a propolis extract, without more detail.

The practitioner today lacks information, which is however essential, on the origin of the extracts and their treatment or transformation, which, for a major part, condition the activity of the food supplement on the one hand, and on the essential active ingredient contents of each of these extracts on the other hand. The practitioner finally also lacks information on the consequences of the combination of these extracts. In fact this lack of information limits the use which may be made of these extracts, as a result, limiting this use to not very characterized products which do not meet present food supplement regulations in effect.

On the contrary, the object of the invention is to propose characterized and reproducible food supplements, allowing use during daily practice, and notably giving to the practitioner, to the physician, the possibility of prescribing a treatment of the food supplement type, alone or in combination with a conventional therapeutic treatment in order to increase the efficiency thereof and to again find the original efficiency thereof.

Thus, a first object of the invention consists of proposing a composition which gets rid of the drawbacks known from the state of the art mentioned above.

Another object of the invention is to propose an antibacterial composition for which the efficiency on the treatment and/or prevention of acute or chronic bacterial infections, and in particular on the treatment of urinary infections, is improved.

Another object of the invention is to propose a composition which allows compensation for a possible zinc and iron deficiency which may occur in men and women respectively.

Another object of the invention is to propose a composition which allows improvement in the bioavailability of vitamin C at nutritional doses while thus avoiding overconsumption of vitamin C.

The object of the present invention is an antibacterial food composition comprising a *Vaccinium macrocarpon* cranberry extract and a propolis extract in which:
  the propolis extract comprises caffeic acid, ferulic acid, galangin and pinocembrin,
  the *Vaccinium macrocarpon* cranberry extract contains a weight proportion of proanthocyanidins (PACs) greater than or equal to 10%, preferably greater than 10%, advantageously comprised between 20 and 50%, said proportion being measured by the vanillin assay method,
the composition being characterized by a propolis extract: *Vaccinium macrocarpon* cranberry extract weight ratio comprised between 1:2 and 2:1.

propolis designates a whole series of resin, gum and balsam substances, with viscous consistency, collected on certain portions, notably the buds and barks of plants, by bees which bring them back to the hive and partly modify them by adding their own salivary secretions and wax. These plants are mainly trees such as pine trees, fir trees, spruces, poplar trees, alders, willows, horse chestnut trees, birches, plum trees, ash trees, oak trees or further elms.

By propolis extract is meant a form of propolis which may be applied. It may therefore be non-transformed or treated, or else transformed in the presence notably of a suitable excipient, for example carob, starch or starch derivative, e.g. maltodextrin. propolis may notably appear in the form of a powder. For this, propolis may be mixed with a hydro-alcoholic solution to which an excipient is added, such as maltodextrin or carob powder, as a carrier. The thereby obtained mixture is evaporated and then dried. A propolis extract comprising 18% of propolis and 82% of carob powder is further marketed as propolis PPM 18 by LUSTREL. Another example of a Propolis extract comprising 60% of propolis and 40% of carob is marketed by CLAUDINE VALLEE.

In a preferred embodiment, the propolis extract weight content in the composition according to the invention is comprised between 10 and 80%, preferably between 30 and 70%.

The *Vaccinium macrocarpon* cranberry extract is preferably obtained by a method for concentrating the total extract of polyphenolic fractions from *Vaccinium macrocarpon* cranberry juice.

*Vaccinium macrocarpon* cranberry juice is drawn from a fruit essentially grown in the North of the United States, as well as in Canada. This juice of dark red color and with an astringent flavor is rich in polyphenols and notably in proanthocyanidins in the free glycosylated form (galactoside, rhamnoside, glucoside) or free esterified form (gallate) such as for example prodelphinidin, propetunidin, promalvidin or procyanidin. These compounds generally exist in polymerized form (dimers to hexamers) and have a chaining of type A or type B according to the two following diagrams, corresponding to the structures of a dimer of type B and of a dimer of type A:

a) dimer of type B

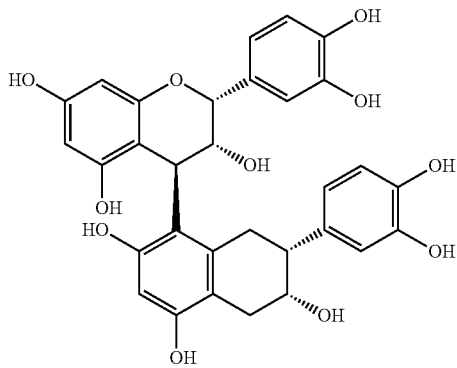

b) dimer of type A

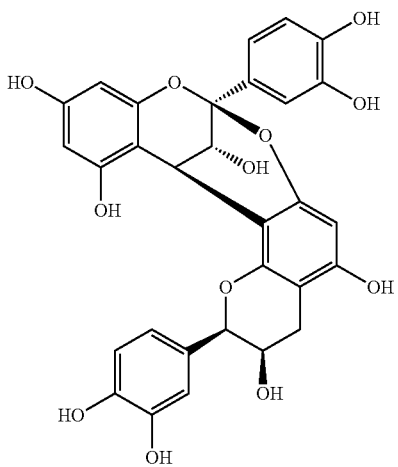

The method for concentrating and isolating polyphenolic fractions of *Vaccinium macrocarpon* cranberry juice notably consists of removing inert substances such as fibers, sugars and fruit acids from the *Vaccinium macrocarpon* cranberry juice by chromatography on an ion exchange resin. This method binds the polyphenols and thus leaves all the inert substances present in the juice, non-adsorbed.

The ion exchange resin preferably consists in a non-ionic polymeric resin, such as the resin marketed under the name of AMBERLITEO® XAD 16 HP by ROHM & HAAS. The latter consists of an aliphatic cross-linked styrene/divinylbenzene copolymer and appears in the form of translucent white beads retaining humidity (62-70%). It has a specific surface area of 800 m$^2$/g and a porosity of ≥0.55 mL/mL. This type of resin is neutral and is suitable for any pH range. The volume size of the pores is about 1.082 mL/g and the average size of the pores is about 100 Å.

Other resins such as Amberlite XAD 4, Amberlite XAD 16 or Amberlite XAD 2 marketed by ROHM & HAAS may also be used.

It is then proceeded with elution of the polyphenols. The ethanol allows gradual elution of the polyphenols without altering them and the recovery of the eluate is continued until the violet coloration in the eluate disappears. An assay of the polyphenols in the eluate is preferably carried out in order to make sure that the totality of the polyphenols has actually been eluated.

According to a particular embodiment of the method, the rinsing of the column is carried out with water in order to remove the compounds not retained by the resin. The rinsing of the column is stopped when the dry material level in the eluate is less than 1%.

The eluate may undergo freeze-drying or atomization thereby giving the possibility of obtaining a *Vaccinium macrocarpon* cranberry extract in the form of a powder.

The proportion of proanthocyanidins (PACs) of the *Vaccinium macrocarpon* cranberry extract is measured by the vanillin assay method.

The principle of this assay is based on the binding of the aldehyde of vanillin on carbon no. 6 of the cycle A of the catechin in order to form a red chromophore complex which absorbs at 500 nm. The vanillin reacts with the catechic monomers and the terminal units of the PACs while it does not react with the intermediate units of the PACs given that their carbon no. 6, binding site for vanillin, is taken in the monomer-monomer bond ($C_4$-$C_6$).

X mg of *Vaccinium macrocarpon* cranberry extract (about 20 mg for a powder or 50 mg for a liquid) are weighed and they are then diluted in 100 mL of water at pH 2 (the pH being adjusted with 37% hydrochloric acid (HCl) by using a pH meter). 1 ml of *Vaccinium macrocarpon* cranberry extract solution is introduced into a 15 ml test tube with a ground glass stopper. At this volume, between 3 and 12 ml of vanillic reagent comprising 4% of vanillin in methanol and between 3 and 12 ml of 37% concentrated hydrochloric acid (HCl) (BURNS 1971) are successively added to this volume. The obtained solution is stirred for 20 mins at 30° C. in a water bath. After 20 mins, the absorbance A at 500 nm of the solution is measured by using as a compensation liquid a solution identical with the solution for which the absorbance A is measured and in which the vanillic reagent is replaced with pure methanol. A standard range is prepared by using catechin. For this, 3 catechin solutions are prepared by respectively weighing 5 mg, 10 mg and 15 mg which are introduced into a 100 ml graduated vial with methanol, each of these 3 solutions being stable for one day. The assay of the standard is carried out on 1 ml of each of the solutions of the standard range by proceeding in the same way as for the sample. The content of total proanythocyanidins expressed as a catechin equivalent for 100 g of *Vaccinium macrocarpon* cranberry extract powder is calculated with the following formula:

$$[proanthocyanidins]\% = \frac{100 \times [catechin\ eq.]}{\frac{x}{0.1}}$$

With:
[proanthocyanidins] content of proanthocyanidins,
[catechin eq.] obtained by determination of the equation of the absorption curve of 500 nm of the solution comprising the *Vaccinium macrocarpon* cranberry extract by linear regression,
x: *Vaccinium macrocarpon* cranberry extract mass A *Vaccinium macrocarpon* cranberry extract comprising 20% of PACs is further marketed under the name of Exocyan CRAN 20S by Tournay Biotechnologies.

In a particular embodiment, the *Vaccinium macrocarpon* cranberry extract weight content in the composition according to the invention is comprised between 10 and 80%, preferably between 25 and 70%.

In another embodiment, the composition according to the invention also comprises a compound selected from the group formed by pharmaceutical actives, food ingredients and nutrients.

In a preferred embodiment, the food ingredient is selected from the group formed by zinc and its derivatives.

In a preferred embodiment, the zinc derivatives are selected from zinc salts such as zinc citrate, zinc oxide, zinc sulfate, zinc acetate or zinc gluconate.

In a preferred embodiment, the weight content of zinc or of one of its derivatives in the composition according to the invention is comprised between 0.01 and 2%, preferably between 0.1 and 1.5%.

In another preferred embodiment, the food ingredient is selected from the group formed by iron and its derivatives.

In a preferred embodiment, the iron derivatives are selected from iron salts, such as iron sulfate, iron lactate, iron gluconate, iron chloride or iron fumarate.

In a preferred embodiment, the weight content of iron or of one of its derivatives in the composition according to the invention is comprised between 0.05 and 3%, preferably between 0.5 and 2.5%.

In another embodiment, the food ingredient is selected from the group formed by ascorbic acid commonly designated as vitamin C and its derivatives.

In a preferred embodiment, the vitamin C derivatives are selected from the salts of ascorbic acid, such as calcium ascorbate, magnesium ascorbate, potassium ascorbate or sodium ascorbate.

In a preferred embodiment, the ascorbic acid salt is calcium ascorbate.

In a preferred embodiment, the weight content of vitamin C or of one of its derivatives in the composition according to the invention is comprised between 1 and 10%, preferably between 2 and 8%.

The weight contents in the composition according to the invention of zinc and of its derivatives, of iron and of its derivatives as well as of vitamin C and of its derivatives observe the daily intakes recommended for each of them. The composition according to the invention characterized by these weight contents may thus represent between 50 and 85% of the daily recommended intakes of zinc, iron or vitamin C.

The composition according to the invention may further comprise a non-toxic excipient or an inert carrier. As an inert excipient, mention may be made of sugars such as lactose or fructose, of cellulose, calcium carbonate, tricalcium phosphate, magnesium phosphate, calcium stearate, magnesium stearate, talcum or colloidal silica AEROSIL® 100 or AEROSIL® 200 marketed by Degussa). As carriers, mention may further be made of compounds which promote urinary excretion such as for example fumitory extract or orthosiphon extract.

The composition according to the invention may also comprise a compound selected from the group formed by polyols such as glycerol or sorbitol, coloring agents, sweeteners such as sucralose or aromatic actives such as fruit aromas.

The composition according to the invention appears as a solid or a liquid.

In a particular embodiment, the composition according to the invention appears as a powder, as gelatin capsules, as capsules, as chewing gums, as granules, as granulates, as cachets, as pills, as lozenges, as caplets or tablets. The galenic application is carried out under conditions of temperatures and pressure which observe the integrity of the applied ingredients and the bioactivity of the active ingredients.

The compositions according to the invention are firstly intended to develop a favorable physiological effect in persons suffering from or subject to bacterial infections, as well as those having asymptomatic bacteriurias or having a risk of asymptomatic bacteriurias, notably pregnant women, elderly women, men suffering from prostate adenoma, disabled persons or persons after a medical diagnostic procedure or a surgical operation. This physiological effect has a favorable effect with which these infections or these bacteriurias may be prevented and/or limited. The most prominent physiological effects are inhibition of bacterial growth, a bactericidal or bacteriostatic effect, an effect for decreasing the adhesion of bacteria, in particular of enterobacteria.

According to an embodiment of the invention, the composition has a so-called "bacterioflush" effect. By a so-called "bacterioflush" effect or a so-called "flushing" effect is meant any effect by which the bacteria are removed from the body via natural routes.

The compositions according to the invention are particularly useful in persons suffering from bladder or urinary infections, for example women with a risk or history of cystitises, in particular pregnant women. Men suffering from benign prostate adenoma, in particular of more than 50 years of age, as well as persons suffering from buccal, gastric and/or respiratory infections or further persons suffering from urinary stases, in particular elderly or disabled persons.

The anti-adhesion effect is particularly of interest for intervening early during an infection and decreasing the bacterial load by the bacteria removal effect, or further for decreasing the risk of occurrence of an infection in sensitive subjects. The composition may also have a decreasing effect on the virulence of P pili bacteria, by reducing the expression of these pili.

In a particular embodiment, with the composition according to the invention it is possible to decrease the expression of virulence genes of uropathogenic bacterial strains and therefore decrease the virulence of such strains. For example the composition according to the invention allows decrease of the expression of the papG3 gene.

A second object of the present application therefore relates to the use of a composition according to the invention for reducing the expression of the virulence genes of pili bacteria P, notably uropathogenic bacteria and more particularly *Escherichia Coli*.

The composition according to the invention is notably characterized by an anti-adhesion effect which is maintained over time, for up to 24 hours. One of the explanations put forward for explaining this effect is the potentialization of the anti-adhesion effect of the PACs present in the *Vaccinium macrocarpon* cranberry extract by the propolis extract.

The invention also relates to a composition comprising a propolis extract and a *Vaccinium macrocarpon* cranberry extract, for simultaneous, separate administration or spread out over time, for treating and/or preventing acute or chronic bacterial infections or asymptomatic bacteriurias and notably bladder or urinary infections.

The invention also relates to a treatment method comprising separate, simultaneous administration or spread out over time, orally in a mammal, notably a human, of a composition comprising a propolis extract and of a composition comprising a *Vaccinium macrocarpon* cranberry extract, for treating and/or preventing acute or chronic bacterial infections or asymptomatic bacteriurias, and notably bladder or urinary infections.

The invention actually also provides the use of a composition comprising a propolis extract for preceding, supplementing or following the use of a composition comprising a *Vaccinium macrocarpon* cranberry extract.

In a particular embodiment, the invention may appear as a kit comprising
- a first composition comprising a propolis extract,
- a second composition comprising a *Vaccinium macrocarpon* cranberry extract.

Depending on the administered dose, the compositions may also have a pharmacological effect.

A third object of the present application relates to a food supplement or a drug comprising a composition according to the invention for treating and/or preventing acute or chronic bacterial infections or asymptomatic bacteriurias.

In a preferred embodiment, the food supplement or the drug according to the invention is intended for treating and/or preventing bladder infections or urinary infections.

In another preferred embodiment, the food supplement or the drug according to the invention is intended for treating and/or preventing buccal, gastric or respiratory infections.

In another preferred embodiment, the food supplement or the drug according to the invention is intended for treating and/or preventing bladder or urinary infections associated with a possible zinc deficiency in men, in particular in men of more than 50 years of age, notably suffering from benign prostate adenoma.

In another preferred embodiment, the food supplement or the drug according to the invention is intended for treating and/or preventing bladder or urinary infections associated with a possible iron deficiency in women, in particular in women with a risk or history of cystitises and notably in pregnant women.

In another preferred embodiment, the food supplement or the drug according to the invention is intended for treating and/or preventing urinary stases in elderly or disabled persons.

In another preferred embodiment, the food supplement or the drug according to the invention is intended for treating and/or preventing acute or chronic bacterial infections and for reinforcing the immune system.

A fourth object of the present application relates to treatment methods comprising the oral administration in a mammal, notably a human, of a composition according to the invention for treating and/or preventing acute or chronic bacterial infections or asymptomatic bacteriurias.

In a preferred embodiment, the treatment method comprises the oral administration of a composition according to the invention for treating and/or preventing bladder infections or urinary infections.

In a preferred embodiment, the treatment method comprises oral administration of a composition according to the invention for treating and/or preventing buccal, gastric or respiratory infections.

In a preferred embodiment, the treatment method comprises oral administration of a composition according to the invention for treating and/or preventing urinary or bladder infections associated with possible zinc deficiency in men, in particular in men of more than 50 years of age, notably suffering from benign prostate adenoma.

In a preferred embodiment, the treatment method comprises oral administration of a composition according to of the invention for treating and/or preventing urinary or bladder infections associated with possible iron deficiency in women, in particular in women with a risk or history of cystitises, notably in pregnant women.

In a preferred embodiment, the treatment method comprises oral administration of a composition according to the invention for treating and/or preventing urinary stases in elderly or disabled persons.

In a preferred embodiment, the treatment method comprises oral administration of a composition according to the invention for treating and/or preventing acute or chronic bacterial infections and for reinforcing the immune system.

This treatment may be associated with an antibacterial therapeutic treatment, notably with administration of an antibiotic, such as ofloxacin (fluoroquinolone), ceftriaxone and cefixime (cephalosporin), β-lactamines and nitrofurad-antin (nitrofurantoin). The object of the invention is therefore the use of the composition according to the invention for preceding, supplementing and/or following an antibacterial therapeutic treatment. This means that the practitioner prescribes to the patient who is in need thereof the consumption of the food supplement or the drug according to the invention as a cure before, during and/or after conducting a treatment with an antibacterial agent, for example an antibiotic.

The object of the invention is also a so-called flash treatment, consisting of participating in the removal of germs resistant to ATB (antibiotherapy) but also of significantly reducing the bacterial population by a flushing effect (water flushing effect). The bacteria are discharged through natural routes and the phylogenetic expression of the adhesion system and more particularly the virulence expression of the pili of type P are reduced.

A daily effective dose of the composition according to the invention is administered. By daily effective dose is meant a dose of the composition according to the invention consumed over a period of 24 hours.

By effective daily dose is notably meant an amount of the composition according to the invention which comprises between 300 and 1,200 mg of *Vaccinium macrocarpon* cranberry extract and between 400 and 2,000 mg of propolis extract.

The object of the invention is further a composition comprising a propolis extract and a *Vaccinium macrocarpon* cranberry extract and a pharmaceutical active ingredient, for example an antibacterial, antibiotic, antioxidant agent such as vitamin C and its derivatives or a food ingredient such as zinc, iron and their derivatives or a nutrient for simultaneous, separate administration or spread out in time.

Another object of the present application relates to a kit comprising
- a first composition comprising a propolis extract and a *Vaccinium macrocarpon* cranberry extract according to the invention
- a second composition comprising for example an antibacterial, antibiotic, antioxidant pharmaceutical active ingredient such as vitamin C and its derivatives or a food ingredient such as zinc, iron or their derivatives or a nutrient.

The different characteristics shown for the propolis extract and the *Vaccinium macrocarpon* cranberry extract are also applied to the kit according to the invention mentioned earlier.

The different characteristics shown for zinc and its derivatives, iron and its derivatives and vitamin C and its derivatives are also applied to the kit according to the invention mentioned earlier.

Within the scope of the association of the composition according to the invention with different antibiotics, a synergistic effect of propolis in the absence of *Vaccinium macrocarpon* cranberry was discovered with certain classes of antibiotics and notably those used in urinary pathology. This synergy gives the possibility of improving the antibacterial activity of the antibiotic, without having to increase the administered amount thereof.

With this synergy, it is therefore possible to limit or even to reduce in the case of an antibacterial therapeutic treatment, and notably in the case of a treatment of urinary infections, the administered dose of antibiotics as well as the frequency of administration to the patient. It allows reduction of the risks of development of resistance to these antibiotics in this patient.

Another object of the invention is therefore an antibacterial composition comprising a propolis extract and an antibiotic agent, for simultaneous, separate administration or spread out over time.

In the sense of the invention, <<simultaneous>> means that both actives are administered through the same route at the same time (for example they are mixed), <<separate>> means that they are administered through different routes or in different locations, and <<spread out over time>> means that they are separately administered at different instants.

The different characteristics shown for the propolis extract also applied to the invention mentioned earlier.

In the present invention, every time reference is made to an antibiotic, this should mean any antibiotic agent which may be selected from the whole of the known classes of antibiotics, and notably from classes of antibiotics used in urinary pathology, and those for which the association with propolis and/or *Vaccinium macrocarpon* cranberry proves to be useful. Mention may advantageously be made of cephalosporins and more particularly cephalosporins of a third generation such as ceftriaxone or cefixime and fluoroquinolones such as ofloxacin. Mention may also be made of β-lactamines and nitrofuradantin.

The different characteristics shown relating to forms which the composition may assume as well as the additional compounds are also applied to the invention.

Another object of the invention is such a composition for treating and/or preventing acute or chronic bacterial infections or asymptomatic bacteriurias, and notably bladder or urinary infections.

Another object of the invention is a method for antibacterial treatment comprising administration in a mammal, notably a human, of such a composition for treating and/or preventing acute or chronic bacterial infections or asymptomatic bacteriurias and notably bladder or urinary infections.

The object of the invention is therefore the use of a composition comprising a propolis extract in order to precede, supplement and/or follow an antibiotic treatment. This means that the practitioner prescribes the patient who is in need thereof the consumption of the composition comprising the propolis extract as a cure before, during and/or after conducting an antibiotic treatment.

In a particular embodiment, the invention may appear in the form of a kit comprising
   a first composition comprising a propolis extract,
   an antibiotic agent.

The different characteristics shown for the propolis extract and the antibiotic agent as well as those relating to the forms which the composition may assume are also applied to the invention as mentioned earlier.

The present inventions and their different embodiments will be better understood upon reading the examples which follow. These examples are given as an indication, without any limitation.

FIG. 3 illustrates a curve of the bactericidal effect of propolis and of ceftriaxone.

FIG. 4 illustrates a curve of the bactericidal effect of propolis and of cefixime.

EXAMPLE 1

Figure 1:
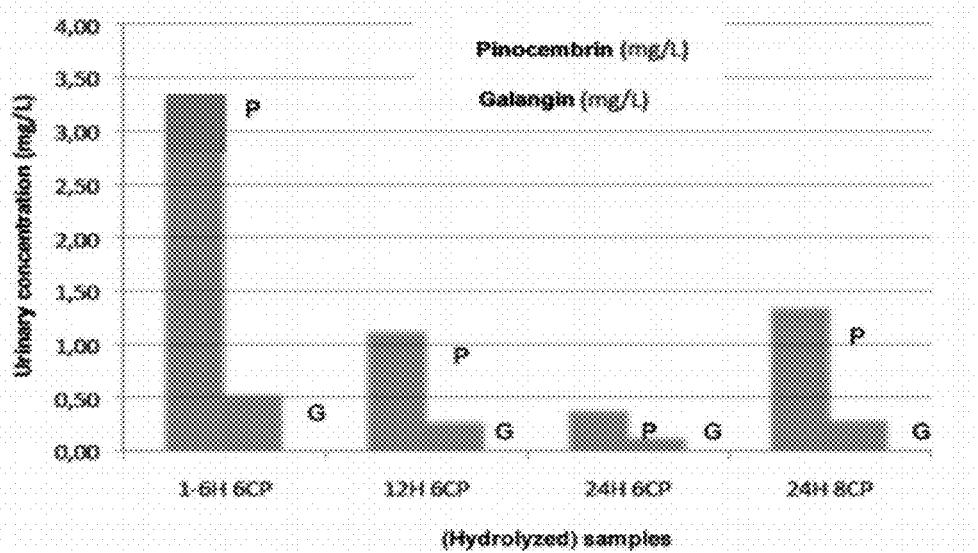
FIG. 1 illustrates the amounts of pinocembrin and galangin present in the propolis extract measured in human urines and after a regimen of 6 and 8 gelatin capsules comprising a composition according to the invention.

Production of a *Vaccinium macrocarpon* Cranberry Extract

A *Vaccinium macrocarpon* cranberry extract comprising at least 20% of PACs is obtained according to Example 1 of patent application EP 1 913 951.

EXAMPLE 2

Production of a Propolis Extract

After having harvested crude propolis, the latter undergoes purification, in order to remove the wax, wood or possible pieces of insects. This purification phase is notably performed by cleaning with suitable solvents, such as alcohol. And then the thereby purified propolis is put into a hydro-alcoholic solution, is filtered, evaporated and then dried. It is then milled and mixed with carob powder as a carrier. The thereby obtained propolis extract appears as a micronized powder of beige color which contains 18% of active material.

EXAMPLE 3

Gelatin Capsules

| | |
|---|---|
| *Vaccinium macrocarpon*[1] cranberry extract | 0.150 g |
| *propolis*[2] extract | 0.250 g |

[1]Exocyan CRAN 20S marketed by Tournay Biotechnologies
[2]*propolis* PPM 18 marketed by Lustrel The composition according to Example 3 appears as a powder and is packaged in gelatin capsules.

EXAMPLE 4

Powder in a Dose Sachet

| | |
|---|---|
| *Vaccinium macrocarpon*[1] cranberry extract | 0.3 g |
| *propolis*[2] extract | 0.5 g |
| Vitamin C | 0.060 g |

[1]Exocyan CRAN 20S marketed by Tournay Biotechnologies
[2]*propolis* PPM 18 marketed by Lustrel The powder is packaged in sachets and the usage dosage is from 2 to 4 sachets per day for 2 to 7 days.

The powder may also be packaged in gelatin capsules and the usage dosage is from 2 to 4 gelatin capsules per day for 2 to 7 days, to be renewed if need be.

EXAMPLE 5

Gelatin Capsules

| | |
|---|---|
| *Vaccinium macrocarpon*[1] extract of cranberry | 0.150 g |
| *propolis*[2] extract | 0.250 g |
| Vitamin C | 0.030 g |

[1] Exocyan CRAN 20S marketed by Tournay Biotechnologies
[2] *propolis* PPM 18 marketed by Lustrel The composition according to Example 5 appears as a powder and is packaged in gelatin capsules and the usage dosage is from 2 to 4 gelatin capsules per day during the risk period, to be renewed if need be.

EXAMPLES 6 AND 7

Compositions Intended for Treating and/or Preventing Bladder Infections and Zinc Deficiencies in Men

| | Example 6 | Example 7 |
|---|---|---|
| *Vaccinium macrocarpon*[1] cranberry extract | 0.3 g | 0.150 g |
| *propolis*[2] extract | 0.5 g | 0.250 g |
| Glycerin | qsp | qsp |
| Fructose | qsp | qsp |
| Lactose | qsp | qsp |
| Zinc sulfate | 0.0055 g | 0.0055 g |
| Red fruit flavor | qsp | qsp |

[1] Exocyan CRAN 20S marketed by Tournay Biotechnologies
[2] *propolis* PPM 18 marketed by Lustrel The composition according to Example 6 appears as a powder and is packaged in dose sachets or gelatin capsules.

The usage dosage in dose sachets is from 2 to 4 sachets per day for 2 to 7 days.

The usage dosage in gelatin capsules is from 2 to 4 gelatin capsules per day, to be renewed if need be.

The composition according to Example 7 appears as a powder and is packaged in gelatin capsules.

The usage dosage in a flash treatment is from 4 to 8 gelatin capsules for a maximum period of one week.

The usage dosage in a preventive treatment is from 2 to 4 gelatin capsules for a 15 day period, to be renewed if need be.

EXAMPLES 8 AND 9

Compositions Intended for Treating and/or Preventing Urinary Infections and Iron Deficiencies in Women

| | Example 8 | Example 9 |
|---|---|---|
| *Vaccinium macrocarpon*[1] cranberry extract | 0.3 g | 0.150 g |
| *propolis*[2] extract | 0.5 g | 0.250 g |
| Glycerin | qsp | qsp |
| Fructose | qsp | qsp |
| Lactose | qsp | qsp |
| Iron sulfate | 0.00914 g | 0.00914 g |
| Red fruit flavor | qsp | qsp |

[1] Exocyan CRAN 20S marketed by Tournay Biotechnologies
[2] *propolis* PPM 18 marketed by Lustrel The composition according to Example 8 appears as a powder and is packaged in dose sachets or in gelatin capsules.

The usage dosage in dose sachets is from 2 to 4 sachets per day for 2 to 7 days.

The usage dosage in gelatin capsules is from 2 to 4 gelatin capsules per day to be renewed if need be.

The composition according to Example 9 appears as a powder and is packaged in gelatin capsules.

The usage dosage in a flash treatment is from 4 to 8 gelatin capsules for a maximum period of one week.

The usage dosage in a preventive treatment is from 2 to 4 gelatin capsules for a 15 day period, to be renewed if need be.

EXAMPLES 10 AND 11

Gelatin Capsules

| | Example 10 | Example 11 |
|---|---|---|
| *Vaccinium macrocarpon*[1] cranberry extract | 0.150 g | 0.150 g |
| *propolis*[2] extract | 0.100 g | 0.100 g |
| Cellulose (casing) | qsp | qsp |
| Calcium carbonate | qsp | qsp |
| Magnesium stearate | qsp | qsp |
| Ethylvanillin | qsp | qsp |
| Zinc sulfate | 0.00125 g | |
| Iron sulfate | | 0.00125 g |
| Menthol flavors | qsp | qsp |

[1] Exocyan CRAN 20S marketed by Tournay Biotechnologies
[2] *propolis* extract with 60% of pure *Propolis* marketed by Claudine Vallée The usage dosage of the composition according to Example 10 is of 4 gelatin capsules per day for 5 to 10 days in an attack use and of 2 gelatin capsules per day for 10 days to be regularly renewed in maintenance use.

The usage dosage of the composition according to Example 11 is of 4 gelatin capsules per day for 5 to 10 days in aggressive use and of 2 gelatin capsules per day for 10 days to be regularly renewed in maintenance use.

EXAMPLE 12

Quantification of Propolis Polyphenols in Human Urines after Ingesting a Composition According to the Invention Two healthy volunteers of more than 18 years of age, with efficient contraception and having followed a normal diet, followed a regimen comprising the ingestion of gelatin capsules according to the composition of Example 3.

Two regimens were followed:
taking 6 gelatin capsules,
taking 8 gelatin capsules.

The taking of gelatin capsules was carried out at 8.00 am and the urines were collected by micturition in a sterile flask before ingestion, 1-6 hours after ingestion, 12 hours after ingestion and 24 hours after ingestion.

The collected urines are hydrolyzed by enzymatic hydrolysis (glucuronidase and sulfatase), and the polyphenols are then extracted and purified on Sep-Pack.

The polyphenols of propolis such as pinocembrin and galangin are then characterized and assayed.

The results are shown in Table 1 below as well as in FIG. 1.

TABLE 1

|  | 1-6 h (6 gelatin capsules) | 12 h (6 gelatin capsules) | 24 h (6 gelatin capsules) | 24 h (8 gelatin capsules) |
|---|---|---|---|---|
| Pinocembrin (P) in mg/L | 3.344 | 1.141 | 0.407 | 1.368 |
| Galangin (G) in mg/L | 0.555 | 0.291 | 0.157 | 0.311 |

These results show that the action of propolis present in the composition according to the invention actually takes place in the human urinary system and thus demonstrates the relevance of the use of the composition according to the invention for targeting the treatment of urinary pathologies.

EXAMPLE 13

Study of the Anti-Adhesion Effect of a Composition According to the Invention

Four healthy volunteers of more than 18 years of age, with efficient contraception, having followed a normal diet and not having received any antibiotic treatment within the two preceding weeks and all along the study followed a regimen comprising the ingestion of gelatin capsules according to the composition of Example 3.

Two regimens were followed:
taking of 4 gelatin capsules for 2 volunteers,
taking of 6 gelatin capsules for the other 2 volunteers.

The taking of the gelatin capsules was performed at 8.00 am and the urines were collected by micturition in a sterile flask before ingestion, 1-6 hours after ingestion 12 hours after ingestion for the 2 volunteers having ingested 6 gelatin capsules and 24 hours after ingestion.

Both volunteers having taken 4 gelatin capsules therefore had 3 urinary collections (H0, H1-6 and H24), 6 urines to be analyzed for this regimen. If there were different micturitions (between 1 and 6 hours after the taking), they were mixed in a same flask.

Both volunteers having taken 6 gelatin capsules therefore had 4 urinary collections (H0, H1-6, H12 and H24), i.e. 8 urines to be analyzed for this regimen. If there were different micturitions (between 1 and 6 hours after the taking), they were mixed in a same flask.

Different biological and physico-chemical parameters of the urine samples were determined with the Multistix® system. An abundance of leukocytes and/or erythrocytes and/or a positivity to nitrites would have caused exclusion of the urine sample. These samples were then refrigerated at +4° C., centrifuged at 4,000 g for 15 minutes at +4° C., and then immediately stored at 20° C.

An uropathogenic E. coli strain previously isolated from the urines of a patient having a urinary infection was selected: NECS19923 having fimbrae of the P (papG) type and pili of type-1. This strain was genetically engineered beforehand by inserting a plasmid bearing the gene coding for GFP (green fluorescence protein).

Adhesion experiments were conducted on lines of urothelial cells of the T24 type of human origin (ATCC HTB-4), adapted from Di Martino et al. The bacteria were put into the presence of the urines of the healthy volunteers in a culture medium containing 5% of Luria Bertani (5% (v/v)) for one night at 37° C. with stirring. The bacteria were then centrifuged and resuspended at a concentration of 108 CFU/mL in a McCoy medium and then put into contact with a monolayer of urothelial T24 cells and incubated for 3 hours at 37° C. After 6 washings with PBS (Phosphate Buffered Saline), the cells were fixed with methanol. The slides were then examined in a fluorescence microscope, the bacteria were then viewed in green. The average number of adhesion bacteria per cell was determined by examining 100 urothelial cells and represents an adhesion index (AI). This index is expressed as the median of 4 independent tests.

The results are shown in Table 2 below

TABLE 2

| | AI median [range] | | | |
|---|---|---|---|---|
| | Volunteer 1 (4 gelatin capsules) | Volunteer 2 (4 gelatin capsules) | Volunteer 3 (6 gelatin capsules) | Volunteer 4 (6 gelatin capsules) |
| 0 h | 20.4 [16-26] | 18.6 [15-28] | 23.0 [14-28] | 21.2 [15-25] |
| 1-6 h | 3.7 [2-10] | 2.1 [1-9] | 3.0 [0-5] | 3.1 [0-4] |
| 12 h | | | 2.1 [0-5] | 2.2 [0-5] |
| 24 h | 17.7 [14-22] | 15.8 [11-18] | 16.9 [12-21] | 19.1 [10-25] |

These results show that the composition according to the invention has "immediate" anti-adhesion activity against E. Coli but also that this activity is maintained over time, up to 24 hours.

EXAMPLE 14

Ex Vivo Study of the Composition According to the Invention on the Virulence of a Uropathogenic E. coli Strain Two healthy volunteers of more than 18 years of age, with efficient contraception, having followed a normal diet and not having received any antibiotic treatment within the two preceding weeks and all along the study followed a regimen comprising the ingestion of gelatin capsules according to the composition of Example 3.

Three regimens were followed:
taking of 4 gelatin capsules,
taking of 6 gelatin capsules,
taking of 8 gelatin capsules.

The taking of gelatin capsules was performed at 8.00 am and the urines were collected by micturition in a sterile flask before ingestion, 1-6 hours after ingestion, 12 hours after ingestion and 34 hours after ingestion.

Both volunteers therefore had 4 urinary collections (H0, H1-6, H12 and H24), i.e. 8 urines to be analyzed for this regimen. If there were different micturitions (between 1 and 6 hours after the taking), they were mixed in a same flask.

Different biological and physico-chemical parameters of the urine samples were determined with the Multistix® system. An abundance of leukocytes and/or erythrocytes and/or positivity to nitrites would have caused the exclusion of the urine sample. These samples were then refrigerated to +4° C., centrifuged at 4,000 g for 15 minutes at +4° C., and then immediately stored at 20° C. A "wash-out" period of one week between the changes in regimen was observed.

An uropathogenic *E. coli* strain previously isolated from the urines of a patient having a urinary infection was selected: NECS19923 having fimbrae of the P type (papG) and pili of type 1. This strain was genetically engineered beforehand by inserting a plasmid bearing the gene coding for GFP (green fluorescence protein).

The in vivo study of the cytoxity of *E. coli* was conducted on the model of *Caenorhabditis elegans* according to the method described by Kurz et al., except for the worms used which is a Fer-15 mutant line, which have fertility depending on ambient temperature. The Fer-15 mutants are provided by the Caenorhabditis Genetics Center (USA). In order to synchronize the growth of the nematodes, the eggs were collected by using the hypochlorite method. NGM (Nematode Growth Medium) geloses were inoculated with 10 µl of an 18 hour culture of *E. coli* put into presence of the composition according to Example 3. These geloses were then incubated at 37° C. for 8-10 hours, and then sown with nematodes in the larva stage L4 (20 to 30 per gelose). The geloses were then incubated at 25° C. and the number of living worms was counted every day with a stereomicroscope (Leica MS5). These experiments gave the possibility of establishing survival curves (DL50: Half-life, time and lifetime) and showed the presence, the absence or the reduction of the virulence (cytoxicity) of the *E. coli* strains. For each experiment, the strains were tested on 3 independent experiments and these experiments were repeated 4 times for each test. A nematode is considered as dead when it no longer reacts to contact with a metal ose. The worms which adhere against the wall of the Petri dishes and die were excluded from the analysis. In order to compare the lifetime of the nematodes between the different regimens, the Cox regression model was applied. In order to carry out comparisons per pair, a log rank test was used. The analysis were carried out by means of the software package SAS/ETS® release 9.1 (SAS Institute Inc, Cary, N.C., USA).

The results are shown in the table below

TABLE 3

| Tests | LT50 (days) | LT100 (days) |
| --- | --- | --- |
| Urines T0 | 4.2 ± 0.2 | 7.4 ± 0.6 |
| Urines 4 gelatin capsules T1-6 h | 6.0 ± 0.1 | 11.3 ± 0.7 |
| Urines 4 gelatin capsules T12 h | 5.5 ± 0.2 | 9.3 ± 0.7 |
| Urines 4 gelatin capsules T24 h | 5.0 ± 0.2 | 7.8 ± 0.8 |
| Urines 6 gelatin capsules T1-6 h | 6.3 ± 0.3 | 11.3 ± 0.7 |
| Urines 6 gelatin capsules T12 h | 5.3 ± 0.3 | 9.5 ± 0.5 |
| Urines 6 gelatin capsules T24 h | 5.8 ± 0.2 | 9.0 ± 1.0 |
| Urines 8 gelatin capsules T1-6 h | 6.0 ± 0.1 | 11.8 ± 0.8 |
| Urines 8 gelatin capsules T24 h | 6.3 ± 0.3 | 11.5 ± 0.5 |
| Control strain OP50 | 7.5 ± 0.5 | 13.3 ± 0.7 |

The results show that the composition according to the invention allows reduction in the virulence of an *E. coli* strain and also that this activity is maintained over time.

EXAMPLE 15

Evaluation of the Expression of the papG3 Gene Under the Effect of the Composition According to the Invention An uropathogenic *Escherichia coli* strain isolated during a urinary infection was selected in the laboratory of the INSERM Espri 6 team: this is a strain sensitive to antibiotics: NECC853118, papG3+, phylotype B2.

Urines from healthy volunteers of more than 18 years of age, with efficient contraception, having followed a normal diet and not having received any antibiotic treatment during the two preceding weeks and all along the study, were collected after the following regimens:
placebo
4 gelatin capsules, 1-6 hours after ingestion,
4 gelatin capsules, 12 hours after ingestion,
8 gelatin capsules, 1-6 hours after ingestion,
8 gelatin capsules, 24 hours after ingestion,
each gelatin capsule corresponding to the composition according to Example 3.

Cultivation of the *E. coli* strain in the different collected urines after the different regimens is carried out for 18 hours at 37° C. with stirring.

The expression level of the gene papG3 was determined by quantitative real time RT-PCR (Real Time-Polymerase Chain Reaction). The expression of the transcripts was normalized with the domestic gene coding for GAPDH (Glyceraldehyde-3 Phosphate Dehydrogenase) measured on each sample. In order to prevent degradation of the mRNAs extracted after cell lyses (which may alter the expression of the genes), the total RNAs were isolated in an RNase-free environment by using the RNeasy Protect Mini kit (Qiagen, Hilden, Germany) by following the recommendations of the supplier. The integrity, the purity and the concentration of the extracted mRNAs were measured by spectrophotometry at 260 nm. The purified RNA was kept in sterile water without any RNase in Eppendorf tubes for freezing. The quantification of the samples was carried out on a LC480 (Roche) by using the QuantiTect SYBR Green RT-PCR Kit (Qiagen, Hilden, Germany). The domestic gene gapdh is used as a reference of the experiment and because it has a constant level of expression under the conditions used. The efficiency of the amplification of the target gene and of the reference gene was determined from the amplification of a dilution series of the samples and the PCR conditions were optimized until a comparable efficiency is obtained among the series (efficiency=2). The amplifications of gapdh and of papG3 were carried out in separate tubes by using the same amount of total RNAs. The mRNA amounts of each gene were determined by comparison of the amplification thresholds (CT).

Figure 2:
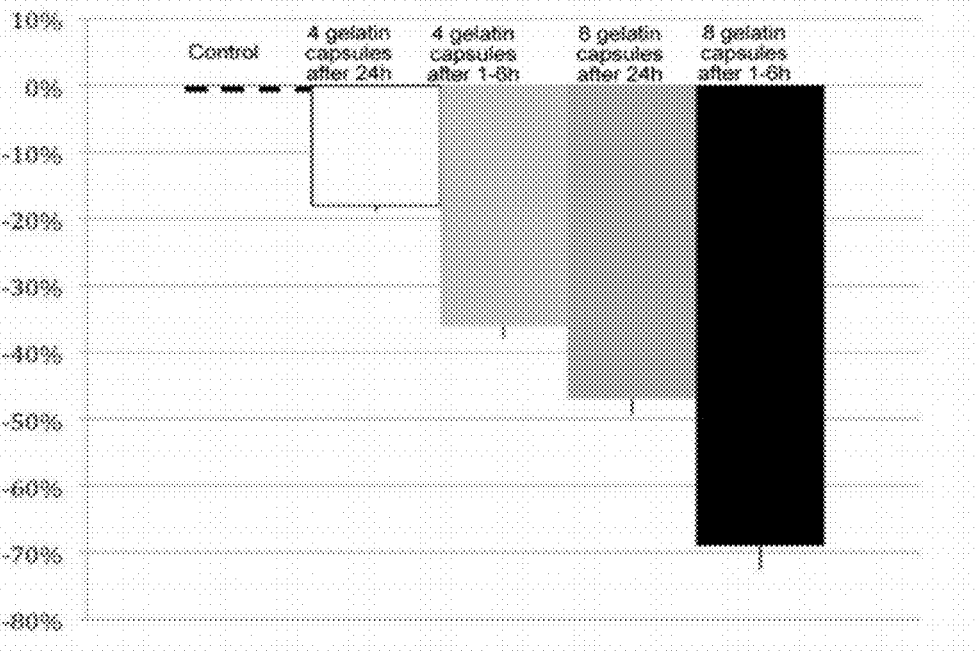
FIG. 2 illustrates the effect of the composition according to the invention on the expression of the papG3 gene of an uropathogenic *E. coli* strain.

The results were expressed by sub/over expression of papG3 relatively to the expression of this gene under normal conditions (*E. coli* in urines without PACs) and are shown in FIG. 2.

As compared with the expression of the gene papG3 detected in the *E. coli* strain put into contact with control urines, this same gene is:
almost 70% (69%) less expressed in the *E. coli* strain put into contact with urines with 8 gelatin capsules of composition according to the invention, taken after 1-6 hours,
almost 50% (47%) less expressed in the *E. coli* strain put into contact with urines with 8 gelatin capsules of composition according to the invention, taken after 24 hours,
35% less expressed in the *E. coli* strain put into contact with urines with 4 gelatin capsules of composition according to the invention, taken after 1-6 hours,
almost 20% less expressed (18%) in the *E. coli* strain put into contact with urines with 4 gelatin capsules of composition according to the invention, taken after 24 hours.

These results show that the composition according to the invention allows reduction in the expression of the gene papG3 and that this activity is maintained over time. They thereby confirm the effect of the composition according to the invention on the decrease in the virulence of E. coli.

EXAMPLE 16

In Vitro Study of the Antibacterial Effect of a Composition According to the Invention and of the Synergy with Different Antibiotic Agents Used in Urinary Pathology Six strains of *Escherichia coli* of different origins (cystitises, acute pyelonephritises, urinary chronic carriage), of different sensitivities to the main antibiotics customarily used in urinary infections and with different virulences, were selected from the strain library of the laboratory of the INSERM Espri 26 team:
- 2 strains sensitive to ATBs: NECS892841 and NECS30090
- 2 strains resistant to quinolones: NECS858785 and NECS864598
- 2 strains secreting BLSE: NEC892420 and NEC118564

Three compositions were evaluated:
- a composition comprising propolis powder on maltose dextrin
- a composition comprising propolis powder on maltose dextrin and PACs of type A
- a composition comprising maltose dextrin Three antibiotics were studied:
- ofloxacin
- ceftriaxone
- cefixime The in vitro study of the antibacterial effect is divided into two steps:
- a step for determining the Minimum Inhibitory Concentration (MIC) of each composition (range of studied concentrations, 0.5 to 5,196 mg/L) and of the antibiotic by a dilution method in a liquid medium according to the recommendations of the CA-SFM (Comité de l'Antibiogramme de la Société Française de Microbiologie) (Antibiogram Committee of the French Microbiology Society).
- a step for determining the MIC of the antibiotic in the presence of each composition in a sub-inhibitory concentration (120 or 250 mg/L depending on the strains) (range of studied concentrations 0.5 to 512 mg/L) by a dilution method in a liquid medium according to the CA-SFM recommendations.

The whole of the tubes were put into an oven at 37° C. overnight without stirring.

The $MIC_{50}$ is the smallest concentration of antibiotic which inhibits any visible culture of a bacterial strain after 18 hours of culture at 37° C.

For ofloxacin, an MIC >1 mg/L is equivalent to a resistant strain.

For ceftriaxone, an MIC >2 mg/L is equivalent to a resistant strain.

For cefixime, an MIC >2 mg/L is equivalent to a resistant strain.

The sensitivity or the resistance to ofloxacin, to ceftriaxone or cefixime is interpreted according to the CA-SFM recommendations.

The results are shown in Tables 4, 5, and 6 below:

TABLE 4

| E. coli strains | Ofloxacin | Ofloxacin + maltose dextrin | Ofloxacin + Propolis | Ofloxacin + Propolis + PAC type A |
|---|---|---|---|---|
| S | 1 | 1 | 0.5 | 0.5 |
| S | 0.25 | 0.25 | 0.06 | 0.06 |
| OFX R | 2 | 2 | 0.5 | 0.5 |
| OFX R | 32 | 32 | 8 | 8 |
| BLSE | >32 | >32 | 8 | 8 |
| BLSE | >32 | >32 | 16 | 16 |

S: a strain sensitive to antibiotics commonly tested against *E. coli*;
OFX R: a strain resistant to ofloxacin;
BLSE: a strain producing b-lactamase with an extended spectrum

TABLE 5

| E.coli strain | Ceftriaxon | Ceftriaxone + maltose dextrin | Ceftriaxone + Propolis | Ceftriaxone + Propolis + PAC type A |
|---|---|---|---|---|
| S | 1 | 1 | 0.125 | 0.125 |
| S | 0.5 | 0.5 | 0.06 | 0.06 |
| OFX R | 0.25 | 0.25 | <0.06 | <0.06 |
| OFX R | 0.5 | 0.5 | 0.06 | 0.06 |
| BLSE | >32 | >32 | 2 | 2 |
| BLSE | 32 | 32 | 2 | 1 |

S: a strain sensitive to antibiotics commonly tested against *E. coli*;
OFX R: a strain resistant to ofloxacine;
BLSE: a strain producing b-lactamase with an extended spectrum

TABLE 6

| E. coli strains | Cefixime | Cefixime + maltose dextrin | Cefixime + Propolis | Cefixime + Propolis + PAC type A |
|---|---|---|---|---|
| S | 1 | 1 | 0.25 | 0.25 |
| S | 0.5 | 0.5 | 0.25 | 0.125 |
| OFX R | 0.5 | 0.5 | 0.125 | 0.125 |
| OFX R | 1 | 1 | 0.125 | 0.25 |
| BLSE | 16 | 16 | 8 | 8 |
| BLSE | 8 | 8 | 2 | 2 |

S: a strain sensitive to antibiotics commonly tested against *E. coli*;
OFX R: a strain resistant to ofloxacine;
BLSE: a strain producing b-lactamase with an extended spectrum.

The results show that the propolis allows improvement in the reactivity of each of the evaluated antibiotics and thus demonstrates a clear synergistic effect of propolis with the 2 classes of antibiotics (cephalosporin, fluoroquinolone) to which belong the evaluated antibiotics.

Moreover, these results also show that the PACs of type A are not detrimental to the activity synergy between propolis and the antibiotic.

EXAMPLE 17

Additional Study of the Synergy between Propolis and Different Antibiotic Agents Used in Urinary Pathology—Bactericidal Effect Curves An isolated strain of *Escherichia coli* during a urinary infection was selected from the strain library of the laboratory of the INSERM Espri 26 team: a strain sensitive to antibiotics NECS892841.

Two compositions were evaluated:
a composition comprising propolis powder on maltose dextrin
a composition comprising maltose dextrin (control)
2 antibiotics are evaluated:
ceftriaxone (CRO)
cefixime (CFM)

The establishment of the antibacterial effect of each composition associated with ceftriaxone is based on the following experiments.

The experiments were conducted in 20 ml of Mueller-Hinton with stirring at 37° C. Each composition was evaluated at 1×MIC (256 mg/L), the ceftriaxone at 0.5×MIC (0.5 mg/L) and the samples were spread out for counting the colonies (CFU) after 0, 1, 2, 3, 5, 6 and 24 hours. A reduction ≥3-log relatively to the original inoculum after 24 hours will be considered as a bactericidal reduction.

The establishment of the antibacterial effect of each composition associated with cefixime is based on the following experiments.

Experiments were conducted in 20 ml of Mueller-Hinton with stirring at 37° C. Each composition was evaluated at 1×MIC (256 mg/L), cefixime at 0.5×MIC (0.5 mg/L) and the samples were spread out for counting the colonies (CFU) after 0, 1, 2, 3, 5, 6 and 24 hours. A reduction ≥3-log relatively to the original inoculum after 24 hours will be considered as a bactericidal reduction.

The counting of the bacterial colonies (CFU) was carried out after 18 hours of culture at 37° C.

The bactericidal effect curves are shown in FIGS. 3 and 4.

The bactericidal effect curves of FIGS. 3 and 4 allow confirmation of the activity synergy between propolis and each of the evaluated antibiotics.

The invention claimed is:

1. A urinary antibacterial oral food composition comprising a *Vaccinium macrocarpon* cranberry extract and a propolis extract, wherein:
the propolis extract comprises caffeic acid, ferulic acid, galangin and pinocembrin and is in the form of a powder with an excipient,
the *Vaccinium macrocarpon* cranberry extract is in the form of a powder and contains a weight proportion of proanthocyanidins (PACs) greater than or equal to 10%, said proportion being measured by the vanillin assay method; and—the propolis extract: *Vaccinium macrocarpon* cranberry extract weight ratio in the composition comprises between 1:2 and 2:1, and
wherein said composition provides active pinocembrin and galangin in the urinary tract and also inhibits bacterial adhesion, bacterial multiplication and bacterial virulence in the urinary tract.

2. The composition according to claim 1, wherein the propolis extract weight content comprises between 10 and 80%.

3. The composition according to claim 1, wherein the *Vaccinium macrocarpon* cranberry extract is obtained by a method for concentrating and isolating polyphenolic fractions from *Vaccinium macrocarpon* cranberry juice.

4. The composition according to claim 1, wherein the *Vaccinium macrocarpon* cranberry extract weight content comprises between 10 and 80%.

5. The composition according to claim 1, wherein it also comprises a compound selected from the group consisting of pharmaceutical actives, food ingredients and nutrients.

6. The composition according to claim 5, wherein the food ingredient is selected from the group consisting of zinc and zinc derivatives.

7. The composition according to claim 6, wherein the zinc derivatives are selected from zinc salts.

8. The composition according to claim 6, wherein the weight content of zinc or of one of zinc derivatives is comprised between 0.01 and 2% of the total weight content of the composition.

9. The composition according to claim 5, wherein the food ingredient is selected from the group consisting of iron and iron derivatives.

10. The composition according to claim 9, wherein the iron derivatives are selected from iron salts.

11. The composition according to claim 9, wherein the weight content of iron or iron derivatives comprises between 0.05 and 3% of the total weight content of the composition.

12. The composition according to claim 5, wherein the food ingredient is selected from the group consisting of vitamin C and vitamin C derivatives.

13. The composition according to claim 12, wherein the vitamin C derivatives are selected from ascorbic acid salts.

14. The composition according to claim 13, wherein the ascorbic acid salt is calcium ascorbate.

15. The composition according to claim 12, wherein the weight content of vitamin C or of one of vitamin C derivatives comprises between 1 and 10% of the total weight content of the composition.

16. The composition according to claim 1 wherein it also comprises a compound selected from the group consisting of sugars, polyols, coloring agents, sweeteners and aromatic actives.

17. The composition according to claim 1, wherein the composition is in the form of a solid.

18. The composition according to claim 1, wherein the *Vaccinium macrocarpon* cranberry extract contains a weight proportion of proanthocyanidins (PACs) greater than 10%.

19. The composition according to claim 1, wherein the *Vaccinium macrocarpon* cranberry extract contains a weight proportion of proanthocyanidins (PACs) comprising between 20 and 50%.

20. The composition according to claim 1, wherein the excipient in the propolis extract powder is selected from the group consisting of carob, starch and a starch derivative.

21. The composition according to claim 1, wherein the excipient in the propolis extract powder is carob.

22. The composition according to claim 1, wherein the excipient in the propolis extract powder is maltodextrin.

23. A food supplement comprising a composition according to claim 1.

24. A drug comprising a composition according to claim 1.

25. A treatment method comprising the oral administration of a composition according to claim 1 for treating and/or preventing acute or chronic bacterial infections or asymptomatic bacteriurias.

26. The treatment method according to claim 25 for treating and/or preventing bladder infections or urinary infections.

27. A composition comprising the composition according to claim 1 and an antibiotic for simultaneous, separate administration or administration spread out in time.

* * * * *